United States Patent [19]

Wuerschum

[11] Patent Number: 5,380,666
[45] Date of Patent: Jan. 10, 1995

[54] METHOD FOR SCANNING AND CENTERING CONTAINERS FILLED WITH A LIQUID

[75] Inventor: Hans-Peter Wuerschum, Ostfildern, Germany

[73] Assignee: Eastman Kodak Company, Rochester, N.Y.

[21] Appl. No.: 51,910

[22] Filed: Apr. 26, 1993

Related U.S. Application Data

[62] Division of Ser. No. 732,254, Jul. 18, 1991, Pat. No. 5,221,519.

[51] Int. Cl.[6] .................. G01N 37/00; B67D 5/00
[52] U.S. Cl. ...................... 436/54; 422/63; 422/65; 422/100; 422/104; 422/107; 436/47
[58] Field of Search .............. 422/65, 66, 63, 64, 422/100, 104, 107; 436/47, 54, 43, 49, 180; 73/864.91

[56] References Cited

U.S. PATENT DOCUMENTS

| | | | |
|---|---|---|---|
| 3,753,657 | 8/1973 | Downing et al. | 422/65 |
| 4,495,975 | 1/1985 | Harstrom et al. | 141/157 |
| 4,534,465 | 8/1985 | Rothermel et al. | 206/443 |
| 4,595,562 | 6/1986 | Liston et al. | 422/65 |
| 4,609,017 | 9/1986 | Coulter et al. | 141/1 |
| 5,008,082 | 4/1991 | Shaw | 422/65 |
| 5,190,727 | 3/1993 | Hirsch | 422/67 |

FOREIGN PATENT DOCUMENTS

| | | |
|---|---|---|
| 384683 | 8/1990 | European Pat. Off. |
| 1921302 | 4/1969 | Germany |

*Primary Examiner*—James C. Housel
*Assistant Examiner*—Long V. Le
*Attorney, Agent, or Firm*—Dana M. Schmidt

[57] ABSTRACT

A method is described for centering and aspirating containers filled with a body fluid and having different diameters, in which the containers are situated on a moveable tray having receptacles for holding a plurality containers of different diameters. The tray is then placed in a pivotable transporter within an analyzer having a scanning and an aspiration station situated along a transport path of the transporter. Scanning elements at the scanning station sense and fix by contact the position of the container and tray respectively so as to locate the center of the container being scanned. Signals from sensing elements aligned with the scanning elements align and position an aspiration probe at the aspiration station to coincide with the centerline axis of the container in order to withdraw all of the body fluid contained therein, regardless of the container diameter.

3 Claims, 6 Drawing Sheets

METHOD FOR SCANNING AND CENTERING CONTAINERS FILLED WITH A LIQUID

This is a divisional application of Ser. No. 732,254, filed Jul. 18, 1991, now U.S. Pat. No. 5,221,519.

FIELD OF THE INVENTION

The invention relates to a device for scanning and centering containers of different diameters filled with a liquid and arranged in a tray, in particular test tubes filled with body fluid and fed to an aspirating station for body fluids in an analyzer.

BACKGROUND OF THE INVENTION

Analyzers featuring automatic scanning and centering means for handling a number of samples or body fluids are known.

A centering means for liquid containers of different diameters that are arranged in a cassette in a single row is known from EP-PA 0 159 346, said means being provided within the cassette in the form of activator means.

In connection with EP-PA 0 159 347, devices for scanning liquid containers in the area of a mixing and aspirating station are known with the position—related to the transport path—of the liquid container relative to the aspirator being detected and the identifications provided on the liquid container being scanned through openings provided in the lateral wall of the cassette. The containers closed by means of stoppers are transported horizontally and moved to an inclined position for liquid removal with the stopper pointing down. For liquid removal the rubber stopper is pierced by a hollow needle of an aspirator.

SUMMARY OF THE INVENTION

It is an object of the present invention to provide a device of the generic type by means of which the different diameters of the containers can be detected, the containers can be centered and fixed in a predetermined position in an aspirating station for body fluids, and the body fluid can be completely removed from the containers regardless of their diameters. Moreover, the processing rate for the samples is to be increased considerably in order to meet the requirements of a quick and reliable diagnosis.

The above object is attained in that the scanning means consists of two movable scanning elements and a sensor that can be covered by said elements.

More particularly, in accord with one aspect of the invention, there is provided a device for centering an aspirating probe in containers of liquid having a center axis, the containers being supported on a tray moved along a support track, the device comprising first position detector means for detecting the position of a container by physical contact, a sensor cooperating with the position detector, and means for generating a signal in response to the contact. The device is improved in that it further includes second position detector means for detecting by contact variations in the position of the tray, and wherein the sensor is operative and positioned to detect both of the position detector means.

In accord with another aspect of the invention, there is provided a device for positioning a container in a tray so that liquid can be accurately aspirated from a centered container, the device comprising first means for detecting and centering by contact a container in a tray. The device is improved in that it further includes second means for centering and fixing by contact the location of a tray relative to an aspirator, the first and second means being constructed to cooperate together.

Expediently, the scanning elements can be moved individually or jointly from an initial position to an end position. Such movement of the scanning elements is advantageously effected in succession.

The invention provides for the sensor to be covered in the initial position by means of the first scanning element and in the end position by means of the second scanning element. Moreover, the scanning elements are advantageously used for centering and fixing the container in a tray and the tray itself on the transport path.

In accord with yet another aspect of the invention, there is provided a method for centering an aspirator probe within a container of liquid, the probe being constructed to descend along an axis having a position adjustable in a horizontal plane depending on the size of the container and the position of the container, the method comprising the steps of a) placing a container of liquid into a tray, the container having a variable diameter;
b) moving the tray and the container of liquid into a position in which the container can be intersected by the probe;
c) sensing and fixing the position of the tray within the horizontal plane and generating a first signal representative of the position;
d) sensing and fixing the center of a container in the tray and generating a second signal representative of the center, and
e) moving the probe so as to descend on a line coincident with the center.

Additional advantageous features of the invention will be apparent in the drawings as well as the following detailed description.

Figure 1:
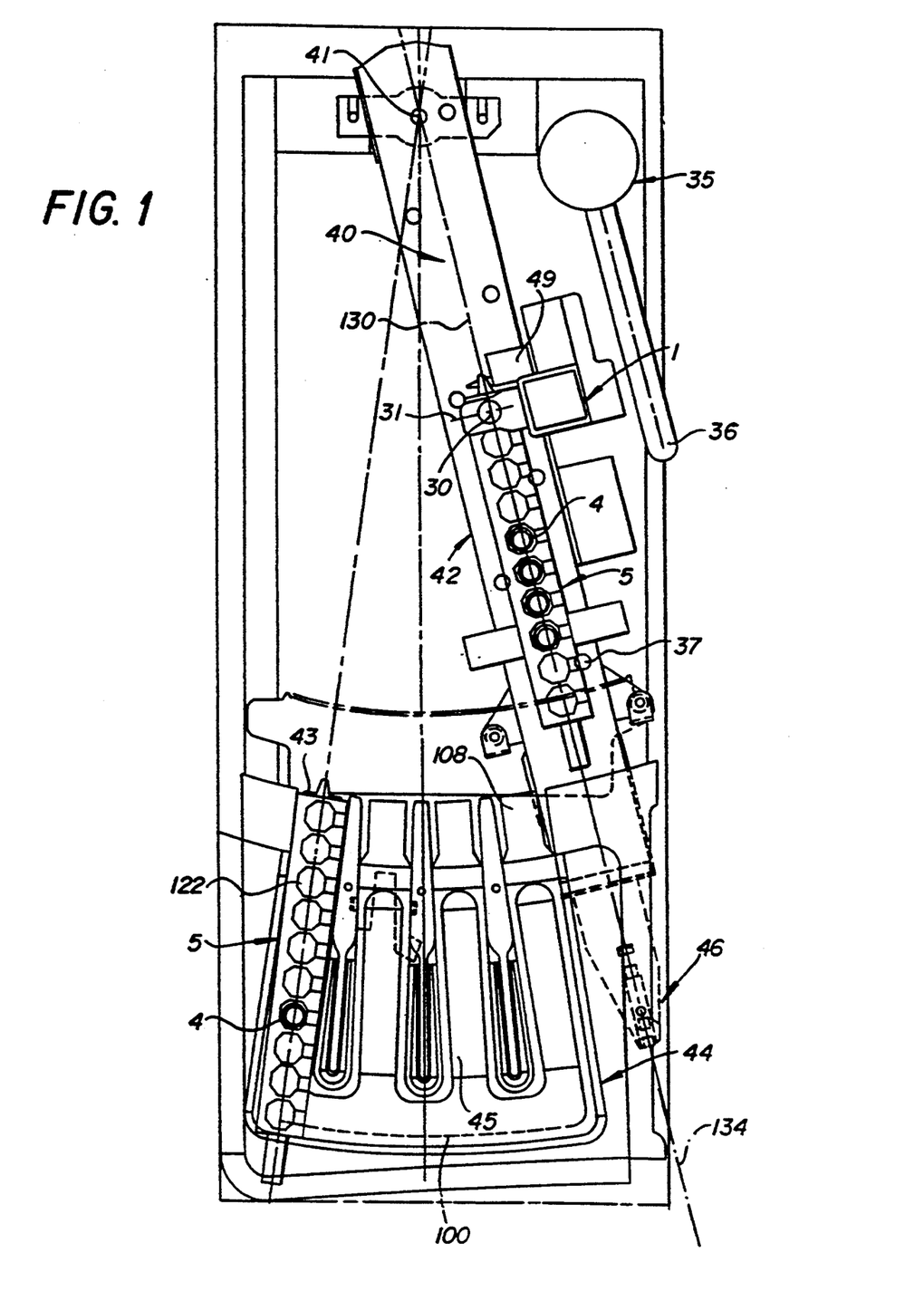
FIG. 1 shows a top view of the device according to the invention comprising a input station, a transport path and two processing stations.

An analyzer illustrated in FIG. 1 consists of an input station comprising four tray tracks 45 arranged side by side for test tubes or elongated trays 5 carrying containers 4, and a transporter 40 which is formed as an elongated housing 42 and is pivotable about a fulcrum 41 so as to be aligned with any of the tray tracks 45 on a support 100. Transporter 40 provides a transport path 130 along its body.

Adjacent to the support 100 for tracks 45 is a zero position 134, which as shown in FIG. 1 is in alignment with path 130. A sensor 46 is mounted on transporter 40, which senses means such as slots, not shown, to determine that path 130 is aligned with position 134.

In accordance with the invention, the analyzer features at zero position 134, a scanning means 1 for scanning the positions of a container 4 and a tray, the scanning means working in cooperation with an aspirating station 30 featuring an aspirator 35 including a proboscis 36 for removing body fluid from a container 4. Aspirating station 30 is arranged so that the path of descent of proboscis 36 intersects the scanning station 46 and the transport path 130, respectively, about halfway down the transport path 130.

The scanning means 1 is arranged adjacent the aspirating station 30 and aligned with its central axis 31 extending normal to the central axis of the transport path 130 when coincident with the zero position 134.

The transport path 130 is about twice as long as a tray 5.

A laterally guided and longitudinally displaceable tray movement member 49 is arranged on the transporter 40 and connected to housing 42, said member being used for moving tray 5 from the input station 44 to the aspirating station 30 and back.

Figure 2:
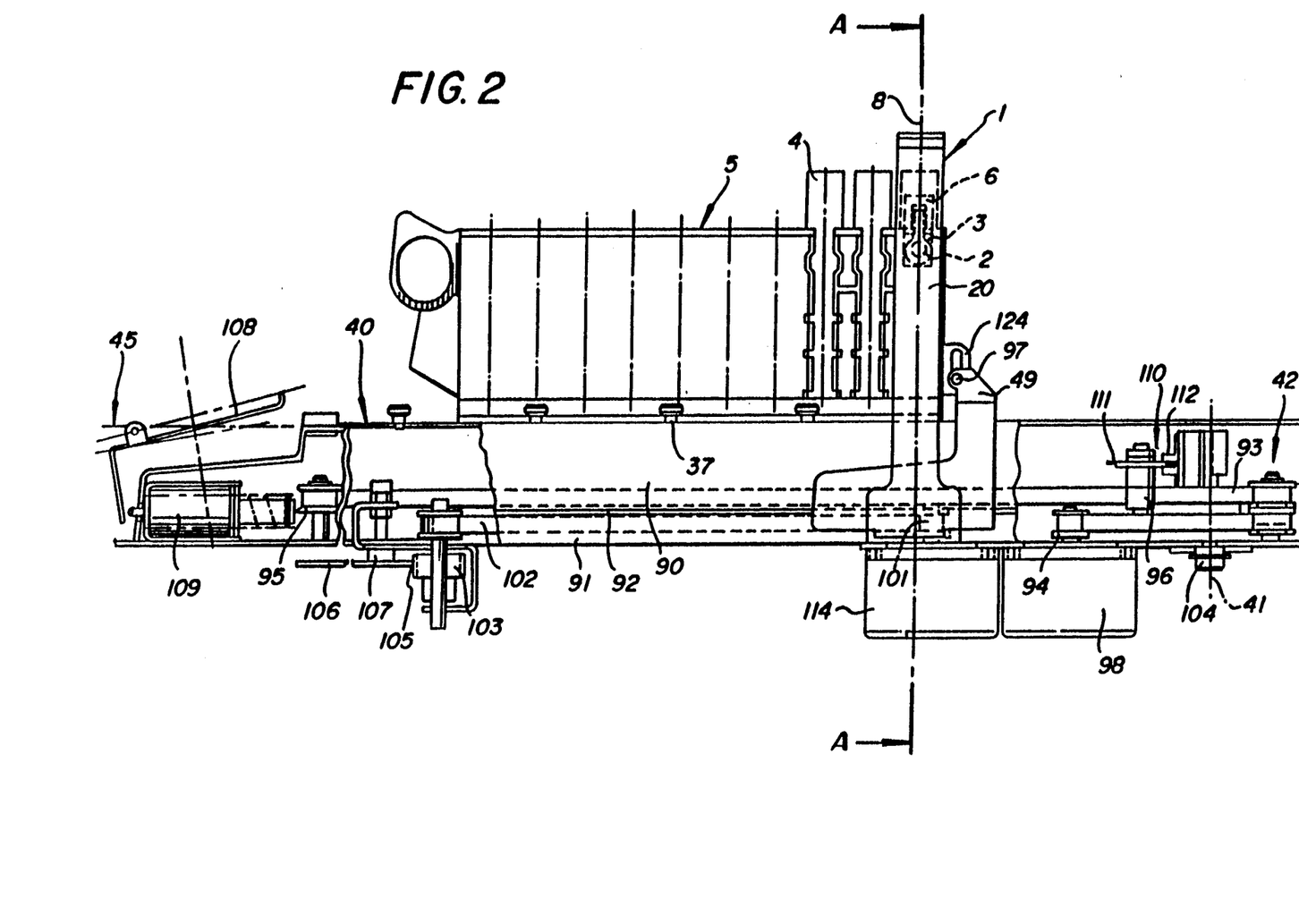
FIG. 2 shows an elevational view of the scanning means according to FIG. 1 including a tray equipped with containers.
Figure 3:
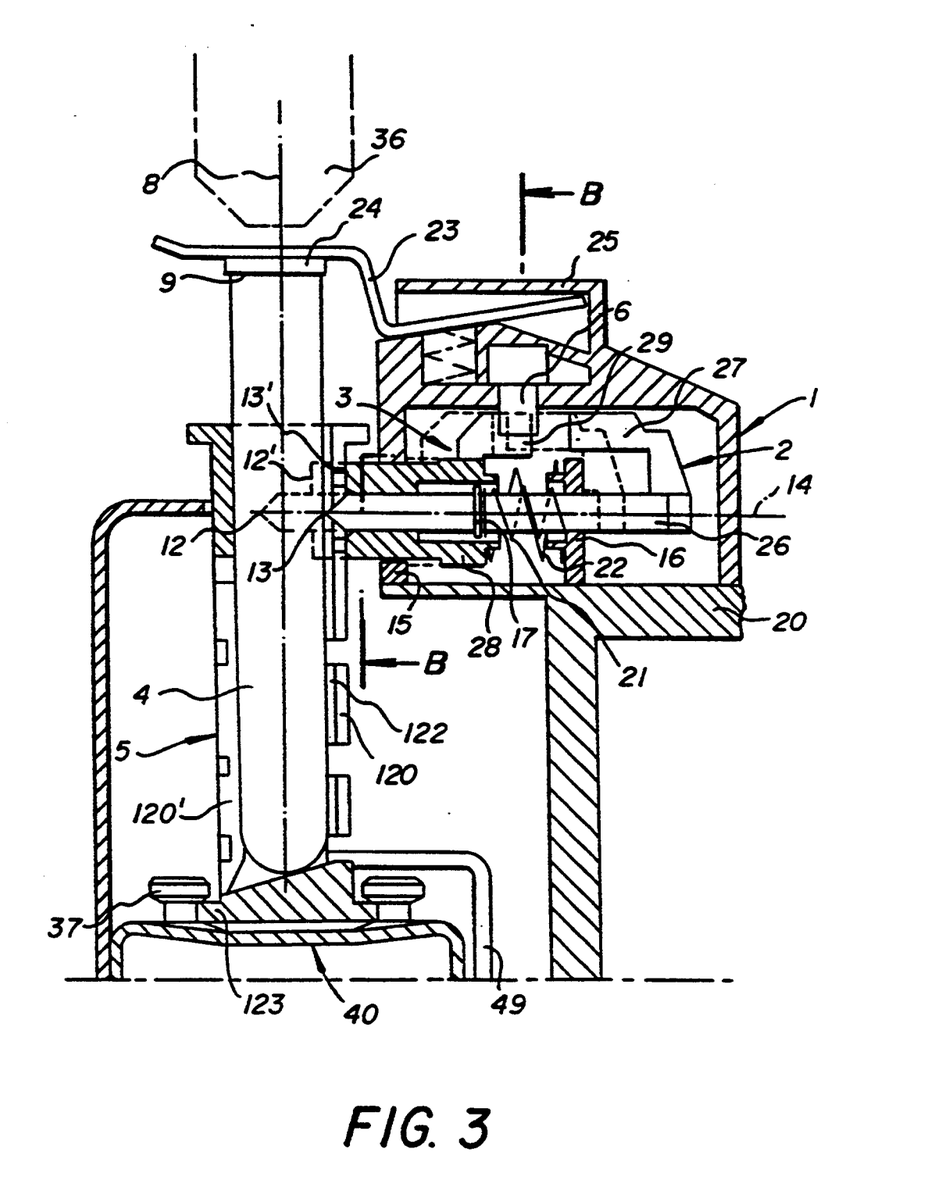
FIG. 3 is a cross-section view along the line A—A in FIG. 2 illustrating the scanning means according to FIG. 1 comprising two scanning elements and a sensor.
Figure 4:
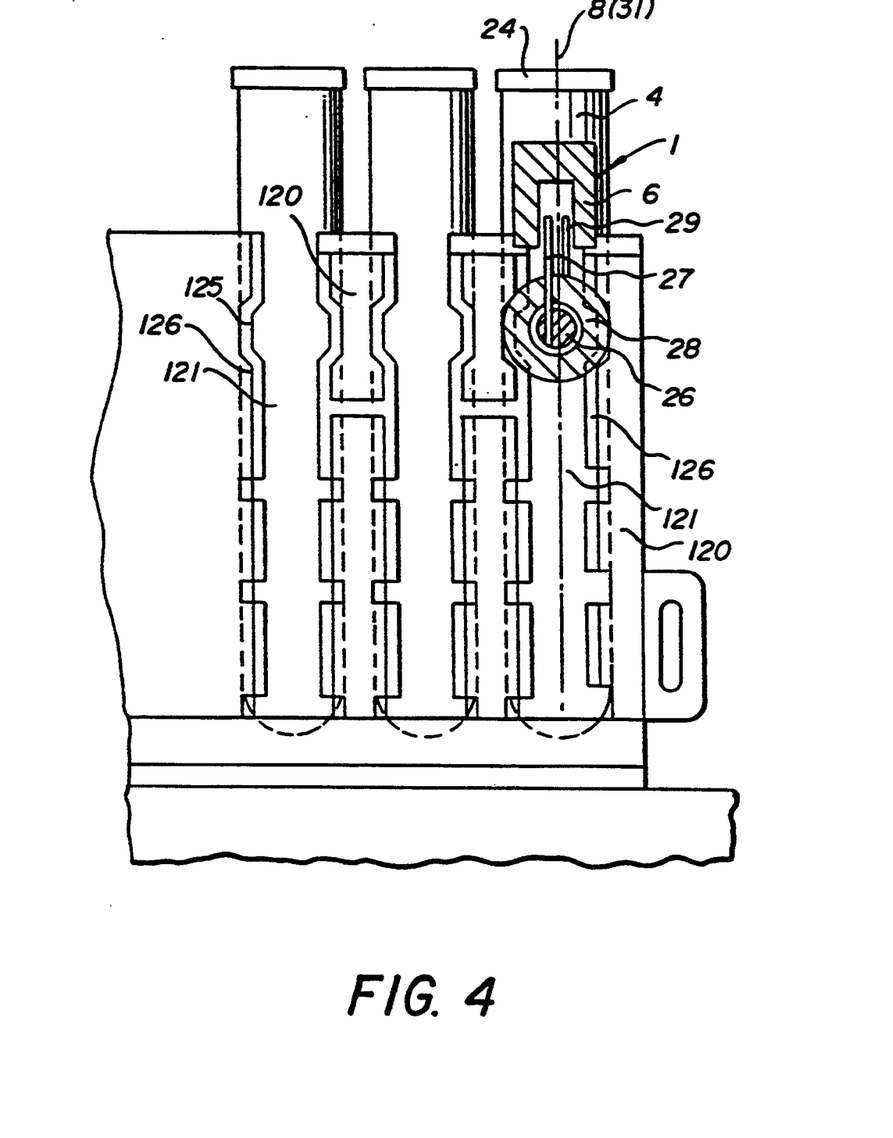
FIG. 4 shows a cross-section view along the line B—B in FIG. 3 illustrating the scanning means according to FIG. 3.

FIGS. 2-4 show the scanning means 1 with a tray 5 positioned on transporter 40 and equipped with containers 4 as well as the tray movement member 49 and its drive elements and a pulse generator 110.

Tray 5 is in a position in which the vertically extending central axis 8 of a container 4 is aligned with the center of the aspirating station 30 and thus with the center of scanning means 1 along the longitudinal side of transport path 130.

Furthermore, FIG. 2 illustrates drive elements for pivoting the transporter 40 whose arrangement and mode of operation will be described in the following.

Housing 42 of transporter 40 is substantially closed on all sides and consists of a housing portion 90 of U-shaped cross-section and a bottom portion 91 of L-shaped cross-section which are connected such that an elongate opening 92 is formed.

With its lower end portion the tray movement member 49 extends through the said elongate opening 92 into the interior of housing 42 and is connected to a toothed belt 93 arranged therein.

Below the bottom portion 91 a stepping motor 98 is arranged which by means of a drive gear 94 and a guide roller 95 drives the toothed belt 93 and thus the tray movement member 49. An encoder wheel 111 is mounted on a drive shaft 96 driven by the toothed belt 93, the rotary movement of said wheel being sensed by a photoelectric switch 112. Encoder wheel 111 and switch 112 represent the pulse generator 110.

At the upper end portion of the tray movement member 49 a hook 97 is arranged which upstream of guide post 37 extends horizontally beyond the centerline of transporter 40 and for transporting tray 5 engages with an eyelet 124 arranged on the front face of tray 5.

Adjacent to the stepping motor 98 an additional stepping motor 114 is mounted to the bottom portion 91 and by means of a drive gear 101 and a toothed belt 102 drives a gear 103 for pivoting the transporter 40 about a journal 104, i.e. fulcrum 41. A gear 103 engages an arcuate rack 104 which in the area of the exits 43 of tray tracks 45 is connected to a support plate 106.

On support plate 106 two supports 107 and 107' are arranged which are mounted to housing 42 of transporter 40 and during pivotable movement of transporter 40 slide thereon.

Each of the exits 43 of tray tracks 45 is associated with a retaining means 108 which is operated by means of an electromagnet 109.

FIG. 3 shows scanning means 1 and tray 5 as well as one of the containers 4 having a lid 24. Scanning means 1 is comprised of a first position detector means 2, a second position detector means 3 and a sensor 6 which are all arranged on a support member 20.

Furthermore, a support member 20 is provided with a cover 25 for the means 2, 3 and the sensor 6, at the upper end portion of cover 25 a vertically pivotable stripper 23 for lid 24 being mounted which in its inoperative position exerts pressure on lid 24 by means of a pressure spring and in the area of the lid has a passageway for proboscis 36 of the aspirator 35 (see FIG. 1).

Means 2 preferably comprises a cylindrical pin 26 which at the end facing container 4 is pointed and at the opposite end has a flag 27. Means 3 preferably comprises a guide member 28 and a flag 29, with said guide member 28 having a bore in its horizontally extending longitudinal axis 14 and flag 29 being arranged at the end portion as in the case of means 2.

Guide member 28 which is shorter than pin 26 of means 2 is slideably supported on pin 26 by means of its bore. At the side of the scanning means 1 facing container 4 guide member 28 is also supported by a support means 15 under cover 25 of support member 20. Along the longitudinal axis 14, pin 26 is also slideably supported by a support means 16 of support member 20, said support means being arranged between flags 27 and 29.

The longitudinal axis 14 common to means 2 and 3 is in alignment with center axis 31 of aspirating station 30, that is to say normal to the vertically extending central axis 8 of container 4 and normal to the longitudinal side of transport path 130 (see FIGS. 1 and 2).

Means 2 and 3 are arranged in the upper area of tray 5 and container 4, respectively. Pin 26 of means 2 extends through guide member 28, projects from scanning means 1 and further extends through an aperture 121 provided in an exterior wall 120 of tray 5. Pressure is thereby exerted on means 2 and 3 by means of spring elements 21, 22. The two spring elements 21, 22 are designed as helical springs coaxially supported by pin 26. One end portion of inner spring element 21 rests on support means 16 and the other on washer 17 permanently connected to pin 26. One end portion of the outer spring element 22 also rests on support means 16 and the other on guide member 28.

In this representation, means 2 and 3 are shown in end positions 13 and 13' determined by the diameter of container 4 and by the width of tray 5.

The pressure forces of spring elements 21, 22 are dimensioned such that container 4 can be centered and fixed in a receptacle 122 of tray 5 and tray 5 itself can be centered and fixed with its widened base 123 on transport path 40 by means of the guide posts 37 provided thereon. For this purpose, receptacle 123 of tray 5 is octagonal in cross-section and thus features for container 4 a prism-shaped nest in an exterior wall 120' (see FIG. 1).

Furthermore, the spring elements 21 and 22 are dimensioned such that means 2 and 3 are positioned in the initial positions 12 and 12' shown in dotted lines when transporter 40 has been pivoted out of scanning station 46.

The initial positions 12 and 12' are thereby limited by means of flags 27 and 29 as well as their positions relative to the support means 16 and 15 associated therewith.

In the initial positions 12 and 12' means 2 projects beyond means 3 by an amount which is larger than the largest admissible radius of a container 4.

The flags 27 and 29 of means 2 and 3 are arranged one behind the other along the longitudinal axis 14 so as to be in alignment with each other and extend vertically upwards into a scanning range of sensor 6.

As shown in the drawing, sensor 6 is covered by flag 29 of means 3 positioned in its end position 13'.

If means 2 and 3 are positioned in the initial positions 12 and 12' when transporter 40 has been pivoted out of scanning station 46, sensor 6 is covered by flag 27 of means 2.

In FIG. 4 means 2, 3 and sensor 6 are shown in cross-section as seen in the direction of their longitudinal axis 14 or in the direction of container 4 held in tray 5.

Pin 26 of means 2 and guide member 28 of means 3 are thereby centrally aligned with the centerpoint of a widened portion 125 of an aperture 121 in the exterior wall 120 of tray 5, the centerpoint being located on central axis 8 of container 4.

Widened portion 125 is arranged symmetrically to aperture 121 and has an octagonal shape. Portion 125 as well as aperture 121 are limited by means of a flange 126 of exterior wall 120. The portion 125 has been adapted to the dimensions of means 2 and 3 such that it is larger than the diameter of pin 26 but smaller than the outer diameter of guide member 28.

As a result, guide member 28 partly covers flange 126 of portion 125 and rests thereon during the scanning procedure (see FIG. 3 and 4).

Sensor 6 is formed by an optoelectric interrupter switch. According to their position along longitudinal axis 14, the flags 27 and 29 mounted at the upper end of means 2 and 3 extend into the scanning range of sensor 6 and pass or interrupt the horizontally extending light beam (see FIG. 3).

The device operates as follows:

For step a) of the method of the Summary, one or several trays 5 equipped with containers 4 or test tubes are inserted in one or all of the four tray tracks 45 of the input station 44. The individual containers 4 are filled with body fluid and generally closed by lids 24.

Figure 5:
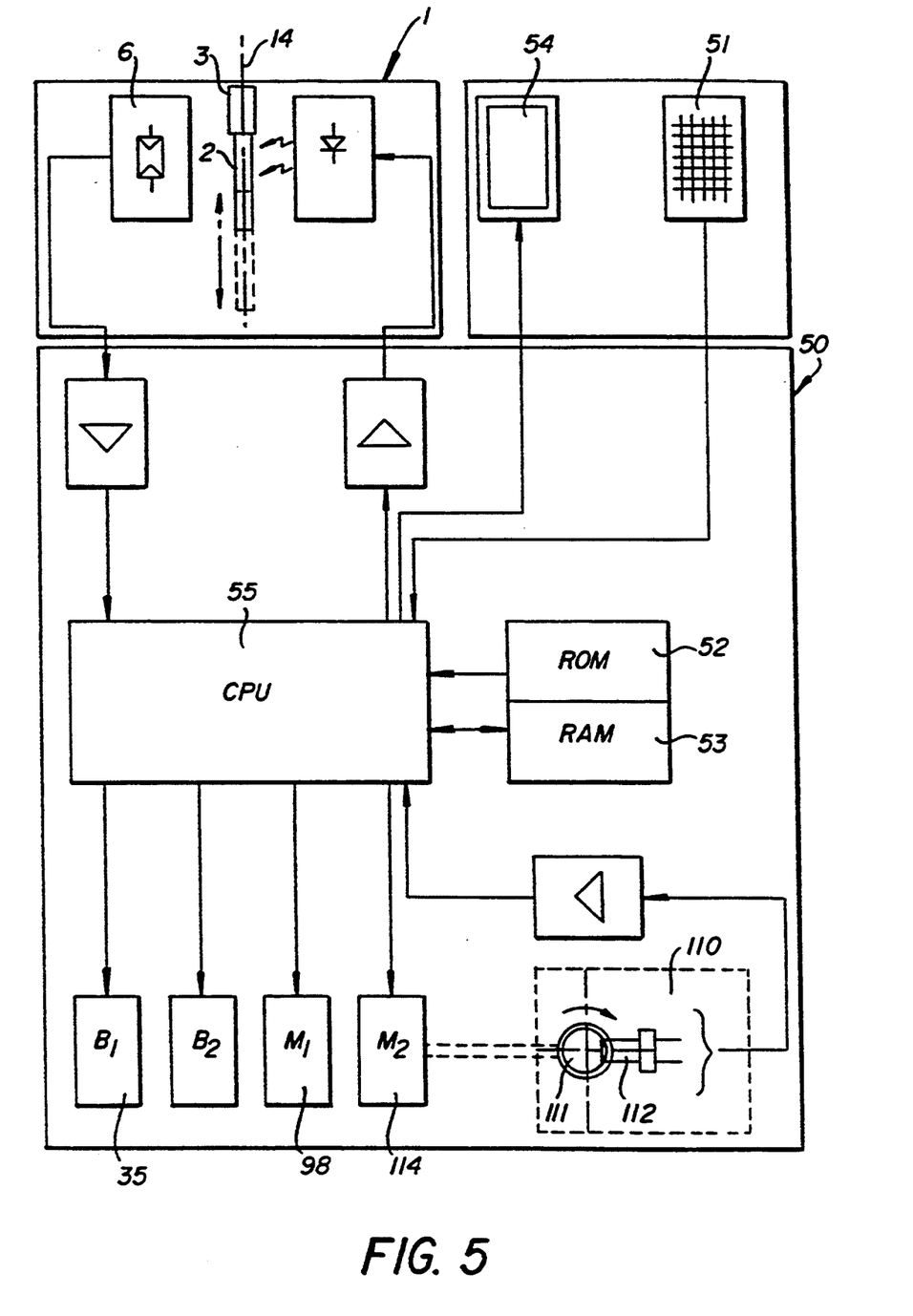
FIG. 5 is a schematic block diagram of a control unit.

If now a processing procedure is started via a keyboard 51 of a control unit 50 shown in FIG. 5, said procedure will proceed according to a program stored in a memory (ROM) 52 and in accordance with the processing instructions of memory (RAM) 53 in cooperation with a microprocessor 55.

After starting the processing procedure, the transporter 40 driven by the stepping motor 114 is pivoted to tray track 45 of input station 44 holding a desired tray 5 with the containers 4 selected.

For step b) of the method set forth in the Summary, tray movement member 49 driven by the stepping motor 98 is moved towards input station 44, with hook 97 engaging eyelet 124 of tray 5 as soon as transporter 40 has reached the tray track 45 selected. When transporter 40 is in alignment with tray track 45, retaining means 108 is removed downwardly from the exit 43 and tray 5 together with the containers 4 is moved onto transport path 130 by the tray movement member 49.

When tray 5 has completely moved onto transporter 40, the transporter is pivoted towards the zero position 134 and thus to the scanning means 1 while tray 5, i.e. the container 4 selected, is simultaneously moved towards the aspirating station 30. The position of container 4 along the transport path 130 is detected in response to tray movement member 49 in that the pulses produced by the pulse generator 110 in proportion to the length of the transport path are counted by the control unit 50.

Pivoting of the transporter 40 and movement of tray 5 are controlled by means of control unit 50 such that the container 4 selected has reached the position of the aspirating station 30 on the transport path 130 before the transport path moves into the line of the zero position 134.

For steps c) and d) of the method, when transporter 40 reaches the zero position 134 and the scanning means 1, first means 2 by means of container 4 and then means 3 by means of tray 5 are moved from their initial positions 12 and 12' to their end positions 13 and 13'. Pivotal movement of transporter 40 is terminated as soon as container 4 is exactly positioned in aspirating station 30 as well as centered and fixed in tray 5 under the action of means 2 and 3.

During the pivotal movement the receiver element of sensor 6 is first uncovered by flag 27 of means 2 and subsequently recovered by flag 29 of means 3 when said means 3 has reached its end position 13'.

Figure 6A:
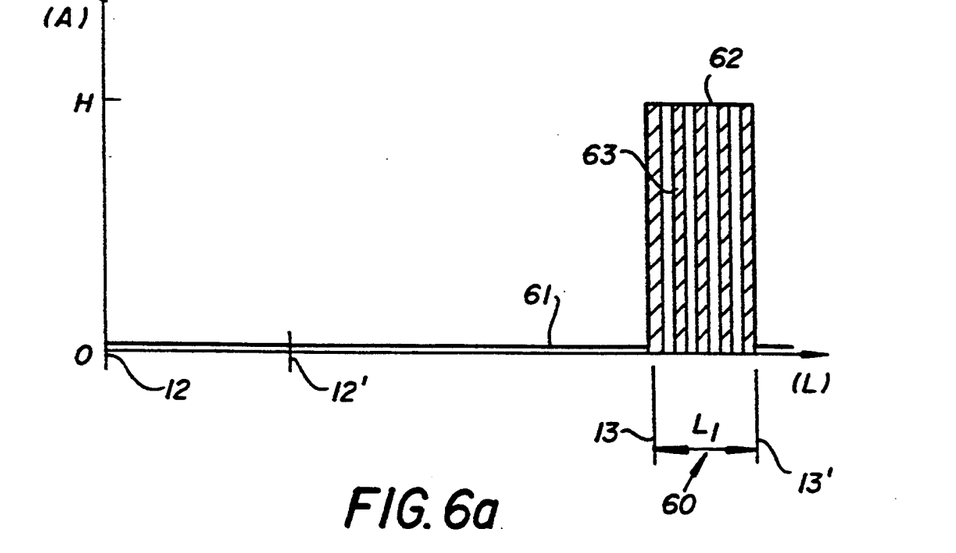
FIGS. 6a and 6b show diagrams indicating the typical signals generated by the sensor according to FIG. 3 in response to the diameters of two different containers.
Figure 6B:
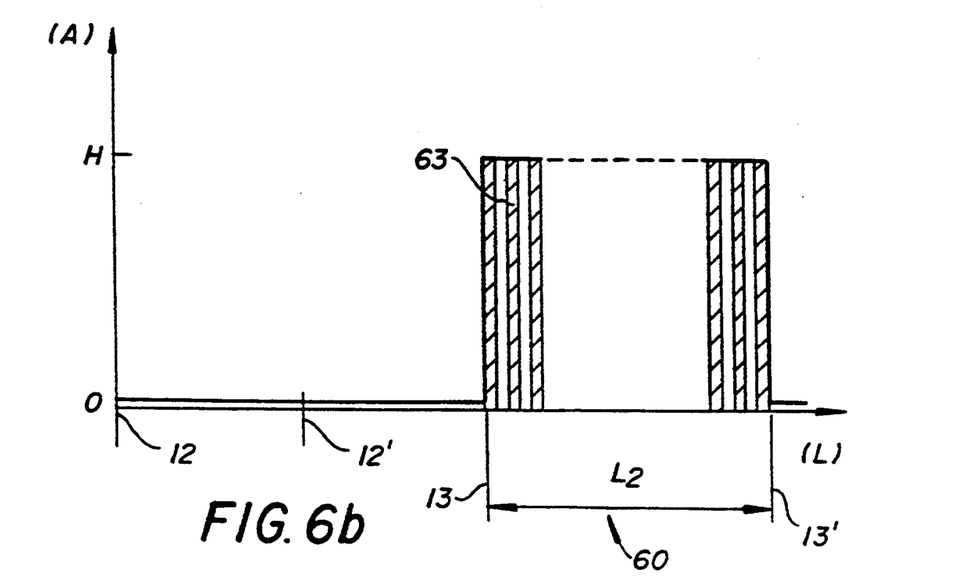

As shown in FIGS. 6a and 6b, the receiver element of sensor 6 produces while being uncovered a signal 62 having a high-level the length 60 of which is determined by the diameter of the scanned container 4. This means that a small diameter relative to a large one produces a shorter signal due to the receiver being uncovered by the means 2 somewhat later, the end position 13' of means 3 being identical with both diameters.

For detecting the diameter (proportional to signal length 60), the stepping pulses 63 of stepping motor 114 of the pivot drive system are counted by the microprocessor 55 of control unit 50 for the duration of the high-level signal 62 and stored in memory (RAM) 53.

Subsequently, for step e) of the method, aspirator 35 is activated by control unit 50 for removal of body fluid from container 4 positioned at the aspirating station 30.

Now the movement of proboscis 36 of aspirator 35 to the center of the opening 9 of container 4 and the dip-in speed and depth of proboscis 36 into the body fluid are controlled in response to the number of stepping pulses 63.

Prior to dipping into the body fluid, proboscis 36 guided through an aperture of stripper 23 pierces the lid 24 placed on container 4.

After removal of body fluid, proboscis 36 is moved to its upper initial position. During this upward movement the lid 24 clinging to the proboscis 36 is stripped off by the stripper 23 and replaced on container 4. Body fluid adhering to proboscis 36 is thereby removed by means of the lid and returned into container 4.

When the proboscis 36 has been pivoted away, transporter 40 controlled by control unit 50 is pivoted out of the scanning station 46 and, according to the program, the next container 4 is moved to the position of transport path 130 corresponding to the aspirating station 30.

During this procedure, transporter 40 is pivoted back to the zero position 134 and the above described process is repeated until the required body fluids have been removed from all containers 4 of tray 5.

Then tray 5 containing the emptied containers 4 is returned to its tray track 45 of input station 44 and the next tray 5 from a further tray track 45 is moved onto the transporter 40.

If tray 5 is incorrectly equipped, that is to say if a container 4 is missing, sensor 6 is not uncovered by means 2 and 3 and thus no signal is produced. This leads to an error message by the control unit 50 indicated on a display panel 54 (see FIG. 5).

What is claimed is:

1. A method for centering an aspirator probe within a container of liquid having a size and position that can vary from container to container, said probe being constructed to descend along an axis having a position adjustable in the horizontal plane depending on the size and the position of the container, the method comprising the steps of:
   a) placing a container of liquid into a tray, said container having a diameter that can vary from container to container;
   b) moving said tray and said container of liquid into a position in which said container can be intersected by said probe;
   c) sensing the position of said tray within said horizontal plane and fixing said tray in said sensed position;
   d) sensing a center of said container in said fixed tray and fixing said container at said sensed center, and
   e) moving said probe so as to descend on a line coincident with said center.

2. A method of aspirating a quantity of liquid from a container having a quantity of liquid contained therein, said method comprising the steps of:
   a) placing a loaded tray of containers having varying diameters into one of a plurality of first positions;
   b) moving a loaded tray from one of said first positions to a second position for aspirating liquid from containers contained within the moving tray;
   c) sensing the location of said tray at said second position and fixing said tray at said sensed location;
   d) sensing a container within said fixed tray to locate a center of said container and fixing said container at said sensed location, and
   e) aspirating liquid from the center of said fixed container.

3. A method as claimed in claim 2 wherein said plurality of first positions and said second position are accurately arranged about a common pivot point and in which step b) further comprises the step of pivoting said loaded tray about said common pivot point to move said loaded tray from one of said first positions to said second position.

* * * * *